United States Patent [19]

Nakayama et al.

[11] Patent Number: 5,093,480
[45] Date of Patent: Mar. 3, 1992

[54] AZOXY COMPOUNDS

[75] Inventors: Masahito Nakayama, Kodaira; Isamu Watanabe, Higashimurayama; Takeo Deushi, Sayama; Kazuhiro Kamiya, Tachikawa; Hisakatsu Ito, Kawagoe; Masami Shiratsuchi, Musashimurayama, all of Japan

[73] Assignee: Kowa Company, Ltd., Nagoya, Japan

[21] Appl. No.: 499,435

[22] PCT Filed: Oct. 21, 1989

[86] PCT No.: PCT/JP89/01082

§ 371 Date: Jun. 21, 1990

§ 102(e) Date: Jun. 21, 1990

[87] PCT Pub. No.: WO90/04585

PCT Pub. Date: Mar. 5, 1990

[30] Foreign Application Priority Data

Oct. 22, 1988 [JP] Japan .................. 63-265275

[51] Int. Cl.$^5$ .................................. C07C 291/00
[52] U.S. Cl. ..................... 534/566; 534/567; 534/570; 534/572
[58] Field of Search ............ 534/566, 567, 570, 572; 514/149

[56] References Cited

FOREIGN PATENT DOCUMENTS 0080831 7/1976 Japan .................. 534/566
0211557 8/1989 Japan .................. 534/566

Primary Examiner—Marianne Cintins
Assistant Examiner—Jessica H. Nguyen
Attorney, Agent, or Firm—Wendroth Lind & Ponack

[57] ABSTRACT

A novel 2-imino derivative of an antifungal product KA-7367A represented by formula,

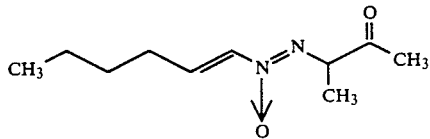

which has high antifungal activity and excellent stability and is useful as an antifungal agent for warm-blooded animals including humans and for agricultural and horticultural usages.

12 Claims, No Drawings

AZOXY COMPOUNDS

TECHNICAL FIELD

This invention relates to a novel azoxy compound, and more specifically to an azoxy compound which is a 2-imino derivative of an antifungal product KA-7367, a process for producing same and its use as an antifungal agent.

TECHNICAL BACKGROUND

The present inventors found before that Streptomyces sp. KC-7367 (FERM BP-1277) separated from a soil in Maniwa-gun, Okayama, Japan produces a product showing high antifunal activity, further isolated two antifungal products, KA-7367A and KA-7367B from the liquid culture medium, and identified and proposed them (refer to Japanese Laid-open Patent Application No. 6248/89, European Patent Laid-open Specification No. 282,001).

Said antifungal products KA-7367A and KA-7367B are represented by the following formula.

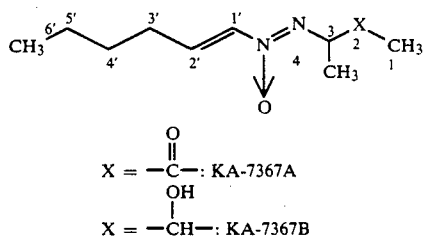

Though the antifungal products KA-7367A and KA-73676B themselves show quite excellent antifungal activity, the present inventors have eagerly made studies to synthesize stable derivatives having by far better antifungal activity, and consequently found that 2-imino derivatives formed by converting a carbonyl group in the 2-position of KA-7367A into an imino exhibit quite high antifungal activity and excellent stability and are useful as antifungal agents; as a result, they have completed this invention.

DISCLOSURE OF INVENTION

This invention is to provide an azoxy compound represented by formula

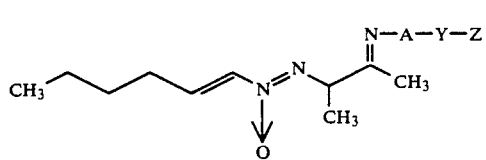

wherein
A denotes —O—, —OCO—, —NH—, —NHCO—, —HNCS— or

Y denotes a single bond or a linear or branched alkylene group with 1 to 6 carbon atoms or a linear or branched alkenylene group with 2 to 6 carbon atoms, and said alkylene or alkenylene group may optionally be substituted by a halogen atom, a phenyl group or a halophenyl group, Z denotes a hydrogen atom, an alkoxy group with 1 to 5 carbon atoms, a carboxyl group, an alkoxycarbonyl group with 2 to 6 carbon atoms, a phenyl group that may optionally have 1 to 3 substituents selected from a halogen atom, an alkoxy group with 1 to 5 carbon atoms, a carboxyl group, a nitro group, a sulfonyl group and a N-methyl-N-alpha-naphthylmethylamino-methyl group, a phenoxy group in which a benzene ring may optionally be substituted by 1 to 3 halogen atoms, a naphthyl group, a cyano group, a pyridyl group, an oxopyridyl group, a imidazolyl group, a furyl group, a thienyl group or a group of formula

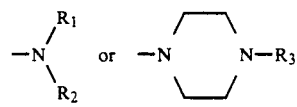

$R_1$ and $R_2$ are the same or different and each denotes a hydrogen atom, an alkyl group with 1 to 3 carbon atoms, a phenyl group, a naphthyl alkyl group, a phenylalkyl group with 7 to 10 carbon atoms, a naphthylalkyl group with 11 to 14 carbon atoms or an amino group, and $R_3$ denotes an alkyl group with 1 to 3 carbon atoms, an alkoxy group with 1 to 3 carbon atoms, a benzoyl group or an alkanoyl group with 2 to 6 carbon atoms that may optionally be substituted by a phenyl group or a halophenyl group, provided when A is the group of formula

is a hydrogen atom,
and its salt.

In the definitions of the substituents in the above formula (I), examples of the linear or branched alkylene group with 1 to 6 carbon atoms include methylene, ethylene, trimethylene, propylene, tetramethylene, ethylethylene, pentamethylene and hexamethylene. Examples of the linear or branched alkenylene group with 2 to 6 carbon atoms are vinylene, propenylene and isoprenylene.

Examples of the halogen atom include fluorine, chlorine, bromine and iodine. Examples of the halophenyl group include o-, m- and p-chlorophenyls, o-, m- and p-fluorophenyls, 2,6-dichlorophenyl, 2,4-dichlorophenyl, 3,4-dichlorophenyl, 2,6-difluorophenyl, 2,4-difluorophenyl, 3,4-difluorophenyl, 2,4,6-trichlorophenyl and 2,4,6-trifluorophenyl.

The alkyl group is linear or branched. Examples thereof include methyl, ethyl, n-propyl and isopropyl.

The alkoxy group is an alkyloxy group whose alkyl moiety is linear or branched. Examples thereof include methoxy, ethoxy, n-propoxy, isopropoxy, n-butoxy, sec-butoxy and tert-butoxy. The alkoxycarbonyl group is an alkyloxycarbonyl group whose alkoxy moiety has the above meaning. Examples thereof include methoxy-carbonyl, ethoxycarbonyl, n-propoxycarbonyl, isopropoxycarbonyl and n-butoxycarbonyl.

Examples of the phenylalkyl group with 7 to 10 carbon atoms include benzyl and phenethyl. Examples of the naphthylalkyl group with 11 to 14 carbon atoms include alpha-naphthylmethyl, beta-naphthylmethyl, alphanaphthylethyl and beta-naphthylethyl. Examples of the alkanoyl group with 2 to 6 carbon atoms include acetyl, propionyl, butyryl, isobutyryl and valeryl.

Preferable examples of the compound of formula (I) provided by this invention are as follows.

(1) Compound of formula (I) wherein
A is —O—,
Y is a single bond, or a linear or branched alkylene group with 1 to 4 carbon atoms or a linear alkenylene group with 2 to 4 carbon atoms that may obtionally be substituted by 1 to 3 halogen atoms or halophenyl groups,
Z is a hydrogen atom, an alkoxy group with 1 to 3 carbon atoms, a carbonyl group, a phenyl group that may optionally have 1 to 2 substituents selected from a halogen atom and a carboxyl group, a cyano group or a group of formula

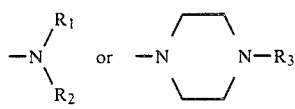

$R_1$ and $R_2$ are the same or different and each is an alkyl group with 1 to 3 carbon atoms, and
$R_3$ is a benzoyl group.

(2) Compound of formula (I) wherein
A is —OCO—,
Y is a single bond or a linear alkylene group with 1 to 4 carbon atoms, and
Z is a hydrogen atom, an alkoxy group with 1 to 3 carbon atoms or a phenyl group that may optionally have 1 to 3 halogen atoms.

(3) Compound of formula (I) wherein
A is —NH—,
Y is a single bond or a linear alkylene group with 1 to 4 carbon atoms that may optionally be substituted by a phenyl group or a halophenyl group,
Z is a hydrogen atom, an alkoxycarbonyl group with 2 to 4 carbon atoms or a phenyl group that may optionally be substituted by a sulfonyl group.

(4) Compound of formula (I) wherein
A is —NHCO—,
Y is a single bond or a linear alkylene or alkenylene group with 1 to 4 carbon atoms which may optionally be substituted by 1 to 3 halogen atoms, phenyl groups or halophenyl groups,
Z is a hydrogen atom, an alkoxy group with 1 to 3 carbon atoms, a phenyl group that may optionally have 1 to 2 substituents selected from a halogen atom, an alkoxy group with 1 to 3 carbon atoms, a nitro group and a N-methyl-N-alpha-naphthylmethylaminomethyl group, a phenoxy group in which a benzene ring may optionally be substituted by 1 to 2 halogen atoms, a naphthyl group, a pyridyl group, an oxopyridino group, an imidazolyl group, a furyl group, a thienyl group or a group of formula

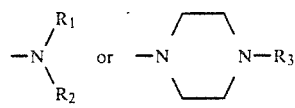

$R_1$ and $R_2$ are the same or different and each is a hydrogen atom, an alkyl group with 1 to 3 carbon atoms, a phenyl group or a naphthyl group with 11 to 12 carbon atoms,
$R_3$ is an alkoxy group with 1 to 3 carbon atoms or an alkanoyl group with 2 to 4 carbon atoms that may optionally be substituted by a halophenyl group.

(5) Compound of formula (I) wherein
A is —NHCS—,
Y is a single bond, and
Z is a group of formula

$R_1$ and $R_2$ are the same or different and each is a hydrogen atom, an alkyl group with 1 to 3 carbon atoms, a phenyl group or an amino group.

(6) Compound of formula (I) wherein
A is

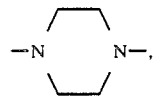

Y is a linear alkylene group with 1 to 4 carbon atoms, and
Z is a hydrogen atom.

Typical examples of the compound in this invention are as follows.

2-Hydroxyimino-2-deoxo-KA-7367A,
2-Methoxyimino-2-deoxo-KA-7367A,
2-(2-Ethoxy-ethoxyimino)-2-deoxo-KA-7367A,
2-Carboxymethoxyimino-2-deoxo-KA-7367A,
2-(1-Carboxy-1-methylethoxyimino)-2-deoxo-KA-7367A,
2-Acetoxyimino-2-deoxo-KA-7367A,
2-Benzoyloxyimino-2-deoxo-KA-7367A,
2-(p-Chlorobenzoyloxyimino)-2-deoxo-KA-7367A,
2-Semicarbazono-2-deoxo-KA-7367A,
2-Thiosemicarbazono-2-deoxo-KA-7367A,
2-Acetylhydrazono-2-deoxo-KA-7367A,
2-(1-Imidazolylacetylhydrazono)-2-deoxo-KA-7367A,
2-(3-Pyridylacetylhydrazono)-2-deoxo-KA-7367A,
2-(2,4-Dichlorophenylacetylhydrazono)-2-deoxo-KA-7367A,
2-(alpha-Naphthylacetylhydrazono)-2-deoxo-KA-7367A,
2-(4-Acetylpiperazinyl-acetylhydrazono)-2-7367A,
2-[4-(2,6-Dichlorophenylacetyl)-1-piperazinyl acetylhydrazono]-2-deoxo-KA-7637A,
2-[(2,6-Difluorophenyl)acetylhydrazono]-2-deoxo-KA-7367A,
2-[2,6-Dimethoxyphenyl)acetylhydrazono]-2-deoxo-KA-7367A,
2-(2-Furylcarbonylhydrazono)-2-deoxo-KA-7367A, 2-Thenoylhydrazono-2-deoxo-KA-7367A,
2-Isonicotinoylhydrazono-2-deoxo-KA-7367A,
2-Nicotinoylhydrazono-2-deoxo-KA-7367A,
2-(p-Chlorophenylacetylhydrazono)-2-deoxo-KA-7367A,
2-(2,4'-Dichlorodiphenylacetylhydrazono)-2-deoxo-KA-7367A, and
2-(2,4-dichlorodiphenylacetylhydrazono)-2-deoxo-KA-7367A.

Basic products of the compound in this invention may take a form of acid addition salts. Examples of an acids capable of forming such acid addition salts are inorganic acids such as sulfuric acid, hydrochloric acid, hydrobromic acid, hydroiodic acid, phosphoric acid, carbonic acid and nitric acid; and organic acids such as acetic acid, fumaric acid, malic acid, citric acid, mandelic acid, succinic acid, p-toluenesulfonic acid and methanesulfonic acid. Pharmaceutically, veterinarily, agriculturally or horticulturaly permissible substances may also selectively be used depending on the use of the compound in this invention.

Acid products of the compound in this invention may take a form of salts such as alkali metal salts, e.g. sodium salts and potassium salts, alkaline earth metal salts, e.g. calcium salts and quaternary ammonium salts.

The compound in this invention can be produced by, for example, reacting the antifungal product KA-7367A of formula A wherein X is

with a compound represented by formula $$H_2N-A-Y-Z \qquad (II)$$

wherein A, Y and Z have the above meanings, or its salt, and converting the resulting compound of formula (I) into a salt if required.

The reaction between the KA-7367A product and the compound of formula (II) or its salt can usually be carried out in a suitable solvent and optionally in the presence of a base at a temperature of about $-10°$ C. to a reflux temperature of a solvent, preferably about $5°$ C. to about $100°$ C. Examples of the solvent include alcohols such as methanol, ethanol and isopropanol; halogenated hydrocarbons such as chloroform and methylene chloride; hydrocarbons such as benzene, toluene, xylene and cyclohexane; and ethers such as ether, dioxane and tetrahydrofurane.

Examples of the base that can optionally be used include inorganic bases such as sodium hydroxide, potassium hydroxide, sodium carbonate and potassium carbonate; and orgnaic bases such as triethylamine, pyridine and 4-methylaminopyridine. These bases can be usually 0.1 to 100 equivalents, especially 1 to 10 equivalents per mol of the KA-7367A product.

The proportion of the compound of formula (II) or its salt relative to the KA-7367 product is not strictly limited but can be varied depending on the type, etc. of the compound of formula (II). The compound of formula (II) or its salt is usually 1 to 10 mols, preferably 2 to 5 mols per mol of the KA-7367 product.

The resulting compound of formula (I) can be converted into the acid addition salt, if required, by the reaction with the aforesaid acid.

Isolation and purification of the final compound can be carried out by methods known per se, e.g. chromatography (e.g. silica gel chromatography and silica gel preparative thin layer chromatography), extraction, distillation and crystallization.

The KA-7367A product used as a starting material in the above process is a known product described in European Patent Laid-open Specification No. 282,001.

Examples of the compound of formula (II) include hydroxylamine ($NH_2OH$), o-alkyl-substituted-hydroxylamine ($NH_2-O-Y-Z-$), o-acyl-substituted-hydroxylamine ($NH_2-OCO-Y-Z$), semicarbazide

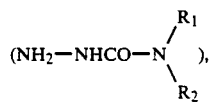

thiosemicarbazide 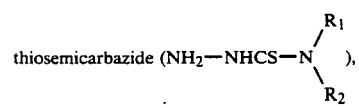

hydrazine ($NH_2-NH_2$), acyl-substituted hydrazine ($NH_2-NHCO-Y-Z$) and N-amino-N'-substituted piperazine

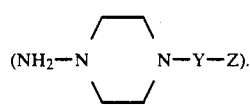

The compound of formula (I) in this invention has high antifungal activity, and exhibits excellent antifungal activity to fungi that infect warm-blooded animals including human, such as Candida, Cryptococcus, Aspergillus, Trichophyton, etc. and fungi that infect agricultural and horticultural crops and fruit trees, such as Piricularia, Botrytis, Saccharomyces, Septoria, etc.

The minimum inhibitory concentrations ($\mu g/ml$), relative to test fungi, of some of the typical compounds in this invention produced in Examples to be described later were measured, and the results are tabulated below.

TABLE 1

| Test Compound (Example No.) | Minimum inhibitory concentration ($\mu g/ml$)* | | | |
|---|---|---|---|---|
| | Test Fungi | | | |
| | Candida albicans | Cystococcus neoformans | Trichophyton mentagrophytes | Trichophyton rubrus |
| 1 | 12.5 | 25 | 12.5 | 3.1 |
| 3 | 25 | 50 | 25 | 6.25 |
| 4 | 12.5 | 25 | 12.5 | 3.1 |
| 5 | 12.5 | 25 | 12.5 | 3.1 |
| 24 | 25 | 50 | 12.5 | 6.25 |
| 25 | 50 | 50 | 12.5 | 3.1 |
| 27 | 100 | 100 | 12.5 | 6.25 |
| 34 | 3.1 | 3.1 | 3.1 | 1.6 |
| 35 | 3.1 | 6.25 | 6.25 | 3.1 |
| 43 | 1.6 | 3.1 | 6.25 | 3.1 |
| 47 | 6.25 | 50 | 25 | 12.5 |
| 48 | 1.6 | 6.25 | 3.1 | 1.6 |
| 49 | 1.6 | 6.25 | 3.1 | 1.6 |
| 52 | 3.1 | 12.5 | 6.25 | 3.1 |
| 53 | 3.1 | 12.5 | 6.25 | 3.1 |
| 54 | 3.1 | 12.5 | 6.25 | 3.1 |
| 61 | 0.8 | 6.25 | 3.1 | 1.6 |
| 62 | 1.6 | 12.5 | 6.25 | 3.1 |
| 67 | 1.6 | 6.25 | 3.1 | 3.1 |
| 68 | 3.2 | 6.25 | 6.25 | 6.25 |
| 70 | 25 | 50 | 25 | 12.5 |
| 71 | 6.25 | 12.5 | 6.25 | 6.25 |
| 74 | 1.6 | 6.25 | 6.25 | 3.1 |

TABLE 1-continued

| Test Compound (Example No.) | Minimum inhibitory concentration (μg/ml)* Test Fungi | | | |
|---|---|---|---|---|
| | Candida albicans | Cystococcus neoformans | Trichophyton mentagrophytes | Trichophyton rubrus |
| 78 | 0.8 | 6.25 | 3.1 | 3.1 |
| 79 | 1.6 | 6.25 | 3.1 | 1.6 |

*The minimum inhibitory concentrations were measured by an agar dilution method using a Sabouraud's dextrose medium in accordance with a standard method of Nippon Kagaku Ryoho Gakkai (Chemical Therapy Academy).

The compound in this invention is low in toxicity. For example, acute toxicities $LD_{50}$ to mice of the compounds in Examples 1 and 4 to be described later are both more than 100 mg/kg (intravenous administration).

It has been confirmed that when KA-7367A is left to stand in serum at 37° C. for 4 hours and then subjected to measurement by thin layer chromatography and biological verification using Candida albicans, it is almost decomposed, whereas the compounds in this invention are little decomposed.

As stated above, the compounds in this invention have excellent antifungal activity to fungi that infect warm-blooded animals including humans and fungi that infect agricultural and horticultural crops and fruit trees, and are useful as antifungal agents for medical, veterinary, agricultural and horticultural usages.

The compounds or their salts in this invention, when used as antifungal agents, can be prepared in dosage forms suited for various usages. For example, when the compounds or their salts in this invention are used as medicines or veterinary drugs (animal drugs), it is possible that adjuvants such as a vehicle, a binder, a lubricant, a disintegrator, a coating, an emulsifier, a suspending agent, a solvent, a stabilizer, an absorption aid, an ointment base, etc. can properly be added thereto and they are prepared into dosage forms for oral administration, administration by injection, subcutaneous injection and external use.

Examples of the preparations for oral administration are granules, tablets, sugar coated tablets, capsules, pills, liquid preparations, emulsions and suspensions. Examples of the preparations for administration by injection are preparations for intravenous injection, subcutaneous injection and instillation. Examples of the preparations for intrarectal administration are suppositories and soft elastic capsules. Examples of the preparations for external use are ointments, lotions, liniments and creams. Dosage forms such as eye drops, ear drops, etc. are also available.

The compounds or their salts in this invention, when used as agricultural and horticultural antifungal agents, can take dosage forms such as liquid preparations, emulsions, granules, powders, dusts and pastes.

The dose of the compound in this invention, when administered to the warm-blooded animals including humans, can vary over a wide range depending on types, conditions, weights and sexes of animals being administered, doctor's judgement, etc. Generally, it is about 0.1 to about 500 mg/kg. weight per day, and the compound can be administered either once or in divided portions a day.

When the compound in this invention is used as an agricultural and horticultural agent, it can be applied to a habitat area of fungi as an agent for soil treatment, an agent for treatment of stems and leaves, etc. Its dose can be e.g. about 0.005 to about 5 kg/ha.

PREFERABLE EMBODIMENTS IN WORKING INVENTION

The following Referential Examples, Examples and Preparation Examples illustrate this invention more specifically.

REFERENTIAL EXAMPLE 1

Streptomyces sp. KC-7367 strain (FERM BP-1277) grown in a potato dextrose agar slant culture medium was inoculated in a liquid culture medium having a composition of 1 % of a soluble starch, 1 % of glucose, 1 % of a soybean powder, 0.5 % of a corn steep liquor, 0.05 % of magnesium sulfate heptahydrate, 0.3 % of calcium carbonate and 0.0005 % of cobalt chloride hexahydrate, said liquid culture medium being adjusted to pH of 7.5. It was cultivated at 28° C. for 2 days to form a seed liquid culture medium.

Ten liters of a liquid culture medium having a composition of 1 % of a soluble starch, 0.5 % of polypeptone S, 0.2 % of a yeast extract, 0.05 % of magnesium sulfate heptahydrate, 0.0005 % of cobalt chloride hexahydrate and 0.2 % of a cotton seed oil, said liquid culture medium being adjusted to pH of 7.5, was charged in a 30-liter jar fermenter. One hundred milliliters of the above seed liquid culture medium was inoculated in said culture medium, and cultivated at a cultivation temperature of 28° C. and an aeration rate of 5 liters/min with 300 rpm for 2 days.

After the cultivation was over, the liquid culture was filtered and 40 liters of the filtrate was adsorbed on Diaion HP-20 column (6×70 cm). After this column was washed with a small amount of a 50 % ethanol solution, elution was conducted with methanol. Fractions having antifungal activity to Candida albicans were gathered and concentrated to dryness under reduced pressure. The residue was dissolved in 200 ml of ethyl acetate, and the solution was washed with 100 ml of a 5 % sodium bicarbonate aqueous solution, 100 ml of 0.02N hydrochloric acid and then 100 ml of water.

An ethyl acetate layer was concentrated to dryness under reduced pressure, and the residue was dissolved in a small amount of methanol and purified by gel chromatography using Toyopearl TSKHW-40 (column: 2×90 cm, eluent: methanol). Active fractions were gathered, concentrated under reduced pressure and developed by preparative thin layer chromatography [eluent: benzeneethyl acetate (10:1)]using silicagel 60F$_{254}$(Merck). Active fractions of Rf0.53 (KA-7367A) and Rf0.22 (KA-7367B) were gathered and eluted with ethyl acetate. The eluate was concentrated under reduced pressure, and the residue was dissolved in methanol. This was purified by gel chromatography (column: 1.5×90 cm, eluent: methanol) using Sephadex LH-20. Active fractions were gathered and concentrated under reduced pressure. There resulted 30 mg of KA-7367A and 3 mg of KA-7367B as colorless oils.

REFERENTIAL EXAMPLE 2

KA-7367B (78 mg) was dissolved in 3 ml of methylene chloride, and 37 mg of pyridinium trifluoroacetate and 243 mg of pyridinium dichromate were added, followed by stirring the mixture at room temperature. Five hours later, 247 mg of pyridinium chromate was added, and the mixture was further stirred at room temperature for 15 hours. To the reaction solution was added 20 ml of diethyl ether, and impurities were removed by suction filtration using celite, followed by concentrating the filtrate under reduced pressure. As a result, 101 mg of a crude oil was obtained. When the crude oil was purified by silica gel chromatography [eluent: benzene-ethyl acetate (50:1)], 19 mg of a colorless oil was provided.

Physicochemical and biological properties of said oil agreed with those of KA-7367A obtained in REFERENTIAL EXAMPLE 1.

EXAMPLE 1

Preparation of 2-hydroxyimino-2-deoxo-KA-7367A

KA-7367A (1.3 g) and 500 mg of hydroxylamine hydrochloride were dissolved in 20 ml of methanol, and 0.3 ml of pyridine was added, followed by stirring the mixture at room temperature for 1 hour. The reaction solution was concentrated under reduced pressure, and extracted with ethyl acetate. The extract was washed with water and then concentrated under reduced pressure. When the concentrate was purified by silica gel column chromatography [eluent: benzene-ethyl acetate (20:1)], 950 mg of a final product (a mixture of a syn-isomer and an anti-isomer) was obtained.

$^1$H-NMR (CDCl$_3$, TMS)δ; 0.94(3H, t, J=7 Hz, 6'-CH$_3$); 1.38, 1.42(total 3H, d, J=7 Hz, 4-CH$_3$); 1.78, 1.96(total 3H, s, 1-CH$_3$); 4.80, 5.38(total 1H, q, J=7 Hz, 3-CH)

EXAMPLE 2

Preparation of 2-methoxyimino-2-deoxo-KA-7367A

The procedure in EXAMPLE 1 was followed except using 70 mg of KA-7367A and 50 mg of o-methylhydroxylamine hydrochloride were treated as in EXAMPLE 1 to obtain 50 mg of a final product (an anti-isomer, containing a very small amount of a syn-isomer).

$^1$H-NMR: (CDCl$_3$, TMS) δ; 0.91(3H, t, J=7 Hz, 6'-CH$_3$); 1.35(3H, d, J=7 Hz, 4-CH$_3$); 1.88(3H, s, 1-CH$_3$); 3.85(3H, s, CH$_3$-O); 4.78(1H, q, J=7 Hz, 3-CH)

EXAMPLE 3

Preparation of 2-(2-ethoxy-ethoxyimino)-2-dioxo-KA-7367A

The procedure in EXAMPLE 1 was followed except using 40 mg of KA-7367A and 40 ml of o-ethoxyethylhydroxylamine to obtain 25 mg of a final product.

$^1$H-NMR: (CDCl$_3$, TMS) δ; 0.92(3H, t, J=7 Hz, 6'-CH$_3$); 1.21(3H, t, J=7 Hz, CH$_3$-CH$_2$—); 1.35, 1.38(total 3H, d, J=7 Hz, 4-CH$_3$); 1.74, 1.93(total 3H, s, 1-CH$_3$); 3.54(2H, q, J=7 Hz, CH$_3$-CH$_2$—); 3.66(2H, q, J=4 Hz, —CH$_2$-CH$_2$—); 4.20(2H, d, J=4 Hz, —CH$_2$-CH$_2$—); 4.78, 5.38(total 1H, q, J=7 Hz, 3-CH)

EXAMPLE 4

Preparation of 2-carboxymethoxyimino-2-deoxo-KA-7367A

The procedure in EXAMPLE 1 was followed except using 100 mg of KA-7367A and 70 mg of aminoxyacetic acid hydrochloride, and the reaction product was purified by silica gel column chromatography [eluent: chloromethanol (20:1)] to obtain 50 mg of a final product.

$^1$H-NMR: (CDCl$_3$, TMS) δ; 0.91(3H, t, J=7 Hz, 6'-CH$_3$); 1.36(3H, d, J=7 Hz, 4-CH$_3$); 1.98(3H, s, 1-CH$_3$); 4.62(2H, S, —O-C$\underline{H}_2$-COOH); 4.77(1H, q, J=7 Hz, 3-CH)

EXAMPLE 5

Preparation of 2-(1-carboxy-1-ethylmethoxyimino)-2-deoxo-KA-7367A

The procedure in EXAMPLE 1 was followed using 100 mg of KA-7367A and 85 mg of aminoxyisobutyric acid hydrochloride. When the reaction product was purified by silica gel column chromatography [eluent: chloroform-methanol (20:1)], 57 mg of a final product was afforded.

$^1$H-NMR: (CDCl$_3$, TMS) δ; 0.91(3H, t, J=7 Hz, 6'-CH$_3$); 1.37(3H, d, J=7 Hz, 4-CH$_3$); 1.50, 1.52(each 3H, s,

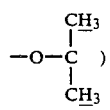

1.97(3H, s, 1-CH$_3$); 4.77(1H, q, J=7 Hz, 3-CH$_3$)

EXAMPLE 6

Preparation of 2-(3-carboxy-2-propenyloxyimino)-2-deoxo-KA-7367A

The procedure in EXAMPLE 1 was followed except using 34 mg of KA-7367A and 26 mg of 4-aminoxycrotonic acid hydrochloride. When the reaction product was purified by silica gel column chromatography [eluent: chloroform-methanol (15:1)], 28 mg of a final product was afforded.

$^1$H-NMR: (CDCl$_3$, TMS) δ; 0.92(3H, t, J=7 Hz, 6'-CH$_3$); 1.36(3H, d, J=7 Hz, 4-CH$_3$); 1.72, 1.95(total 3H, s, 1-CH$_3$); 7.10(1H, m, —C$\underline{H}$=CH-COOH)

EXAMPLE 7

Preparation of 2-(3-carboxy-2-chloro-n-propoxyimino)-2-deoxo-KA-7367A

The procedure in EXAMPLE 1 was followed except using 31 mg of KA-7367A and 29 mg of 4-aminoxy-3-chlorobutyric acid to provide 32 mg of a final product.

$^1$H-NMR: (CDCl$_3$, TMS) δ; 0.92(3H, t, J=7 Hz, 6'-CH$_3$); 1.71, 1.90(total 3H, s, -C$\underline{H}_2$-COOH);

EXAMPLE 8

Preparation of 2-(4-dimethylamino-n-butoxyimino-2-deoxo-KA-7367A

The procedure in EXAMPLE 1 was followed except using 40 mg of KA-7367A and 62 mg of o-(4-dimethylaminobutyl)-hydroxylamine dihydrochloride to provide 12 mg of a final product.

$^1$H-NMR: (CDCl$_3$, TMS) δ; 0.91(3H, t, J=7 Hz, 6'-CH$_3$); 1.36, 1.38(total 3H, each d, J=7 Hz, 4-CH$_3$); 1.87, 2.01(total 3H, each s, 1-CH$_3$); 2.63, 2.67(total 6H, each s,

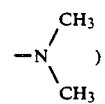

EXAMPLE 9

Preparation of 2-(p-carboxybenzyloxyimino)-2-deoxo-KA-7367A

The procedure in EXAMPLE 1 was followed except using 20 mg of KA-7367A and 21 mg of o-(p-carboxybenzyl)-hydroxylamine hydrochloride to obtain 30 mg of a final product.

$^1$H-NMR: (CDCl$_3$, TMS) δ; 0.91(3H, t, J=7 Hz, 6'-CH$_3$); 1.35, 1.41(total 3H, each d, J=7 Hz, 4-CH$_3$); 1.75, 1.97(total 3H, each s, 1-CH$_3$); 5.15(2H, s,

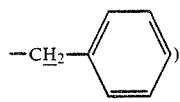

7.42, 8.07(each 2H, d, J=8.5 Hz, aromatic H)

EXAMPLE 10

Preparation of 2-(2,6-dichlorobenzyloxyimino)2-deoxo-KA-7367A

The procedure in EXAMPLE 1 was followed except using 50 mg of KA-7367A and 50 mg of o-(2,6-dichlorobenzyl)-hydroxylamine hydrochloride to afford 55 mg of a final product.

$^1$H-NMR: (CDCl$_3$, TMS) δ; 0.92(3H, t, J=7 Hz, 6'-CH$_3$); 1.35, 1.41(total 3H, each d, J=7 Hz, 4-CH$_3$); 1.70, 1.96(total 3H, each s, 1-CH$_3$); 5.13(2H, s,

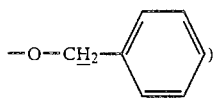

7.2-7.4(3H, m, aromatic H)

EXAMPLE 11

Preparation of 2-(alpha-2,4-dichlorophenylcarboxymethoxyimino)-2-deoxo-KA-7367A

The procedure in EXAMPLE 1 was followed except using 40 mg of KA-7367A and 55 mg of aminoxy-(2,4-dichlorophenyl)-acetic acid hydrochloride to obtain 79 mg of a final product.

$^1$H-NMR: (CDCl$_3$, TMS) δ; 0.91(3H, t, J=7 Hz, 6'-CH$_3$); 1.74, 1.76, 1.95, 1.96(total 3H, each s, 1-CH$_3$); 4.73, 4.75, 5.25, 5.32(total 1H, each 1, J=7 Hz, 3-CH); 7.21(1H, m, aromatic H); 7.41(2H, m, aromatic H)

EXAMPLE 12

Preparation of 2-(4-benzoyl-1-piperazinoethoxyimino-2-deoxo-KA-7367A

The procedure in EXAMPLE 1 was followed except using 100 mg of KA-7367A and 100 mg of o-(4-benzoyl-1-piperzinoethyl)-hydroxylamine to provide 51 mg of a final product.

$^1$H-NMR: (CDCl$_3$, TMS) δ; 0.91(3H, t, J=7 Hz, 6'-CH$_3$); 1.35(3H, d, J=7 Hz, 4-CH$_3$); 1.89(3H, s, 1-CH$_3$); 2.22(2H, q, 3'-CH$_2$—); 2.61(4H, t, piperazine ring 2,6-CH$_2$); 4.19(4H, t, piperazine ring 3,5-CH$_2$); 4.77(1H, q, J=7 Hz, 3-CH-) 6.9-7.1(2H, m. aromatic H)

EXAMPLES 13 to 23

The procedure in EXAMPLE 2 was repeated except using a suitable o-substituted hydroxylamine instead of methoxyamine to obtain a compound of formula:

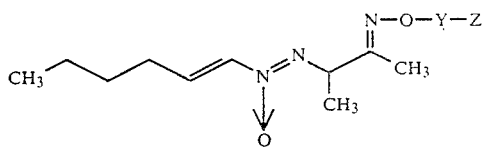

| Example | Y | Z |
|---|---|---|
| 13 | —CH$_2$—CH$_2$— | H |
| 14 | —CH$_2$—CH$_2$—CH$_2$— | H |
| 15 | —CH$_2$—CH(CH$_3$)— | H |
| 16 | —CH$_2$— | phenyl |
| 17 | single bond | " |
| 18 | " | 2-Cl-phenyl |
| 19 | " | 3-Cl-phenyl |
| 20 | " | 4-Cl-phenyl |
| 21 | —CH$_2$—CH$_2$— | —N(CH$_3$)$_2$ |
| 22 | —CH$_2$— | —CN |
| 23 | —CH$_2$—CH$_2$— | " |

EXAMPLE 24

Preparation of 2-acetoxyimino-2-deoxo-KA-7367A

2-Hydroxyimino-2-deoxo-KA-7367A (40 mg) obtained in EXAMPLE 1 and 100 mg of pyridine were dissolved in 6 ml of methylene chloride, and 100 mg of acetic anhydride was added dropwise, followed by stirring the mixture at room temperature for 1 hour. To the reaction solution was added 30 ml of methylene chloride, and the mixture was washed with water, dried and concentrated under reduced pressure. When the concentrate was purified by silica gel column chromatography [eluent: benzene-acetic acid (20:1)], there resulted 26 mg of a final product.

$^1$H-NMR: (CDCl$_3$, TMS) δ; 0.91(3H, t, J=7 Hz, 6'-CH$_3$); 1.41(3H, d, J=7 Hz, 4-CH$_3$); 2.05(3H, s, 1-

CH$_3$); 2.18(3H, s, CO-CH$_3$); 4.91(1H, q, J=7 Hz, 3-CH$_3$)

EXAMPLE 25

Preparation of 2-benzoyloxyimino-2-deoxo-KA-7367A

The procedure in EXAMPLE 24 was repeated except using 120 mg of 2-hydroxyimino-2-deoxo-KA-7367A and 100 mg of benzoyl chloride to provide 110 mg of a final product.

$^1$H-NMR: (CDCl$_3$, TMS) δ; 0.91(3H, t, J=7 Hz, 6'-CH$_3$); 1.47(3H, d, J=7 Hz, 4-CH$_3$); 2.20(1H, q, J=7 Hz, 3-CH); 7.45(2H, m, aromatic H); 7.58(1H, m, aromatic H); 8.05(2H, m, aromatic H)

EXAMPLE 26

Preparation of 2-(o-chlorobenzoyloxyimino)-2-deoxo-KA-7367A

The procedure in EXAMPLE 24 was repeated except using 60 mg of 2-hydroxyimino-2-deoxo-KA-7367A and 60 mg of o-chlorobenzoyl chloride to afford 65 mg of a final product.

$^1$H-NMR: (CDCl$_3$, TMS) δ; 0.92(3H, t, J=7 Hz, 6'-CH$_3$); 1.48(3H, d, J=7 Hz, 4-CH$_3$); 2.18(3H, s, CO-CH$_3$); 5.03(1H, q, J=7 Hz, 3-CH); 7.30-7.50(total 3H, m, aromatic H); 7.83(1H, M, aromatic H)

EXAMPLE 27

Preparation of 2-(p-chlorobenzoyloxyimino)-2-deoxo-KA-7367A

The procedure in EXAMPLE 24 was repeated except using 60 mg of 2-hydroxyimino-2-deoxo-KA-7367A and 60 mg of p-chlorobenzoyl chloride to afford 65 mg of a final product.

$^1$H-NMR (CDCl$_3$, TMS) δ; 0.92(3H, t, J=7 Hz, 6'-CH$_3$); 1.48(3H, d, J=7 Hz, 4-CH$_3$); 2.18(3H, s, CO—CH$_3$); 5.03(1H, q, J=7 Hz, 3-CH); 7.42(2H, m, aromatic H); 7.98(2H, m, aromatic H);

EXAMPLE 28

Preparation of 2-(2,6-dichlorobenzoylimino)-2-deoxo-KA-7367A

The procedure in EXAMPLE 24 was repeated except using 60 mg of 2-hydroxyimino-2-deoxo-KA-7367A and 70 mg of 2,6-dichlorobenzoyl chloride to provide 70 mg of a final product.

$^1$H-NMR: (CDCl$_3$, TMS) δ; 0.92(3H, t, J=7 Hz, 6'-CH$_3$); 1.42(3H, d, J=7 Hz, 4-CH$_3$); 2.16(3H, s, CO—CH$_3$); 5.05(1H, q, J=7Hz, 3-CH); 7.32-7.40(total 3H, m, aromatic H)

EXAMPLES 29 to 33

The procedure in EXAMPLE 25 was repeated except using the other acid halide than benzoyl chloride to obtain a compound of formula:

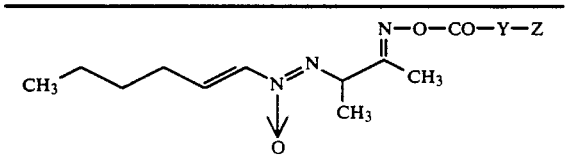

| Example | Y | Z |
|---------|---|---|
| 29 | —CH$_2$— | H |
| 30 | —CH$_2$—CH$_2$—CH$_2$— | H |

-continued

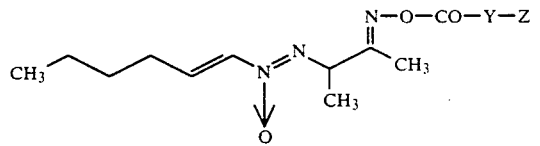

| Example | Y | Z |
|---------|---|---|
| 31 | —CH$_2$—CH(CH$_3$)— | H |
| 32 | single bond | 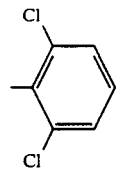 |
| 33 | " | 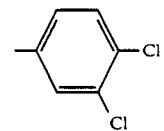 |

EXAMPLE 34

Preparation of 2-semicarbazono-2-deoxo-KA-7367A

KA-7367A (40 mg) and 23 mg of semicarbazide hydrochloride were dissolved in 5 ml of methanol, and 0.1 ml of pyridine was added, followed by stirring the mixture at room temperature for 1 hour. The reaction solution was concentrated under reduced pressure, and the residue was extracted with ethyl acetate. The extract was washed with water and con centrated under reduced pressure. When the residue was purified by silica gel column chromatography [eluent: chloroform-methanol (30:1)], 20 mg of a final product was obtained.

$^1$H-NMR (CDCl$_3$, TMS) δ; 0.92(3H, t, J=7 Hz, 6'-CH$_3$); 1.35(3H, d, J=7 Hz, 4-CH$_3$); 1.90(3H, s, 1-CH$_3$); 4.80(1H, q, J=7 Hz, 3-CH)

EXAMPLE 35

Preparation of 2-thiosemicarbazono-2-deoxo-KA-7367A

KA-7367A (40 mg) and 35 mg of thiosemicarbazide were dissolved in 5 ml of methanol, and stirred at room temperature for 16 hours. The reaction mixture was treated as in EXAMPLE 34 to obtain 20 mg of a final product.

$^1$H-NMR: (CDCl$_3$, TMS) δ; 0.92(3H, t, J=7 Hz, 6'-CH$_3$); 1.38(3H, d, J=7 Hz, 4-CH$_3$); 1.97(3H, s, 1-CH$_3$); 4.77(1H, q, J=7 Hz, 3-CH)

EXAMPLES 36 to 40

The procedure in EXAMPLE 34 or 35 was repeated except using 4-N-substituted semicarbazide or thiosemicarbazide to obtain a compound of formula:

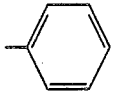

| Example | A | $R_1$ | $R_2$ |
|---|---|---|---|
| 36 | —NHCS— | —CH₃ | —CH₃ |
| 37 | —NHCO— | " | —H |
| 38 | " | " | —CH₃ |
| 39 | " | " | —C₆H₅ |
| 40 | —NHCS— | " | —H |

EXAMPLE 41

Preparation of 2-hydrazono-2-deoxo-KA-7367A

KA-7367A (25 mg) was dissolved in 2.5 ml of methanol, and 1 ml of a 0.2 mol hydrazine-methanol solution was added under ice cooling. The mixture was left to stand at room temperature for 2 hours. The reaction solution was concentrated to dryness and purified by preparative thin layer chromatography (carrier: silica gel, solvent: ethyl acetate) to obtain 5 mg of a final product.

UV: λCH3OH/max, 231 nm

¹H-NMR: (CDCl₃, TMS); 0.92(3H, t, J=7 Hz, 6'-CH₃); 1.36(3H, d, J=7 Hz, 4-CH₃); 1.83(3H, s, 1-CH₃); 2.39(2H, t, J=7 Hz, 3'-CH); 6.96-6.98(2H, m, —CH=CH—)

EXAMPLE 42

Preparation of 2-(4-methyl-1-piperazinoimino-2-deoxo-KA-7367A

The procedure in EXAMPLE 41 was repeated except using 30 mg of KA-7367 and 23 mg of N-amino-N'-methylpiperazine hydrochloride to obtain 8 mg of a final product.

¹H-NMR: (CDCl₃, TMS) δ; 0.92(3H, t, J=7Hz, 6'-CH₃); 1.39(3H, d, J=7Hz, 4-CH₃); 2.01(3H, s, 1-CH₃); 2.29(3H, s, N-CH₃); 2.56(4H, t, J=5Hz, -NCH₂x2); 2.76, 2,98(each 2H, t, J=5Hz, -NCH₂x2); 4.65(1H, q, J=7Hz, 3-CH); 6.96(2H, m, —CH=CH—)

EXAMPLE 43

Preparation of 2-acetylhydrazono-2-deoxo-KA-7367A

The procedure in EXAMPLE 41 was repeated except using 10 mg of KA-7367 and 3.4 mg of acetylhydrazine to provide 10 mg of a final product.

¹H-NMR: (CDCl₃, TMS) δ; 0.92(3H, t, J=7Hz, 6'-CH₃); 1.38(3H, d, J=7Hz, 4-CH₃); 1.88(3H, s, 1-CH₃); 2.25(3H, s, N-COCH₃); 4.80(1H, q, J=7Hz, 3-CH); 6.96(2H, m, —CH=CH—)

EXAMPLE 44

Preparation of 2-chloroacetylhydrazono-2-deoxo-KA-7367A

The procedure in EXAMPLE 41 was repeated except using 40 mg of KA-7367A and 20 mg of chloroacetylhydrazine to afford 13 mg of a final product.

¹-NMR: (CDCl₃, TMS) δ; 0.93(3H, t, J=7Hz, 6'-CH₃); 1.38(3H, d, J=7Hz, 4-CH₃); 1.92(3H, s, 1-CH₃); 4.47(2H, s, Cl-CH₂); 4.77(1H, q, J=7Hz, 3-CH); 6.97(2H, m, —CH=CH—)

EXAMPLE 45

Preparation of 2-trimethylaminoacetylhydrazino-2-deoxo-KA-7367A chloride

The procedure in EXAMPLE 41 was repeated except using 100 mg of KA-7367A and 60 mg of trimethylaminoacetylhydrazine chloride to afford 115 mg of a final product.

¹H-NMR: (CDCl₃, TMS) δ; 0.92(3H, t, J=7Hz, 6'-CH₃); 1.38(3H, d, J=7Hz, 4-CH₃); 1.19(3H, s, 1-CH₃); 3.50(9H, s, NCH₃); 4.90(2H, s, CO—CH₂—N); 6.93(2H, m, —CH=CH—)

EXAMPLE 46

Preparation of 2-benzoylhydrazono-2-deoxo-KA-7367A

The procedure in EXAMPLE 41 was repeated except using 40 mg of KA-7367A and 27 mg of benzoylhydrazine to provide 56 mg of a final product.

¹H-NMR: (CDCl₃, TMS) δ; 0.92(3H, t, J=7Hz, 6'-CH₃); 2.02(3H, s, 1-CH₃); 6.97(2H, m, —CH=CH—) 7.45(3H, m, aromatic H); 7.83(3H, m, aromatic H)

EXAMPLE 47

Preparation of 2-(1-imidazolylacetylhydrazono)-2-deoxo-KA-7367A

The procedure in EXAMPLE 41 was repeated except using 30 mg of KA-7367A and 21 mg of 1-imidazolylacetylhydrazine to provide 13 mg of a final product.

¹-NMR: (CDCl₃, TMS) δ; 0.92(3H, t, J=7Hz, 6'-CH₃); 1.40(3H, d, J=7Hz, 4-CH₃); 1.89(3H, s, 1-CH₃); 5.40(2H, s, CO—CH₂—N); 6.97-7.1(4H, m, —CH=— and imidazole ring H-4.5); 7.53(1H, s, imidazole ring H-2)

EXAMPLE 48

Preparation of 2-(3-pyridylacetylhydrazono)-2-deoxo-KA-7367A

The procedure in EXAMPLE 41 was repeated except using 40 mg of KA-7367A and 35 mg of 3-pyridylacetylhydrazine to provide 62 mg of a final product.

¹-NMR: (CDCl₃, TMS) δ; 0.92(3H, t, J=7Hz, 6'-CH₃); 1.39(3H, d, J=7Hz, 4-CH₃); 1.88(3H, s, 1-CH₃); 3.96(2H, s, CO—CH₃); 7.26(1H, dd, J=8Hz, pyrizine ring H-5); 7.69(1H, td, J=8Hz, 2Hz, pyrizine ring H-4); 8.50(1H, dd, J=5Hz, 2Hz, pyrizine ring H-6); 8.57(1H, d, J=2Hz, pyrizine ring H-2);

EXAMPLE 49

Preparation of 2-(2.4-dichlorophenylacetylhydrzono)-2-deoxo-KA-7367A

The procedure in EXAMPLE 41 was repeated except using 20 mg of KA-7367A and 22 mg of 2,4-dichlorophenylacetylhydrazine to obtain 36 mg of a final product.

$^1$H-NMR: (CDCl$_3$, TMS) δ; 0.91(3H, t, J=7 Hz, 6'-CH$_3$); 1.38(3H, d, J=7 Hz, 4-CH$_3$); 1.87(3H, s, 1-CH$_3$); 4.05(2H, s, CO—CH$_2$); 7.1–7.3(2H, m, aromatic H); 7.38(1H, m, aromatic H)

EXAMPLE 50

Preparation of 2-(3,4-dichlorophenylacetylhydrazono)-2-deoxo-KA-7367A

The procedure in EXAMPLE 41 was repeated except using 30 mg of KA-7367A and 32 mg of 3,4-dichlorophenylacetylhydrazine to provide 59 mg of a final product.

$^1$H-NMR: (CDCl$_3$, TMS) δ; 0.92(3H, t, J=7 Hz, 6'-CH$_3$); 1.39(3H, d, J=7 Hz, 4-CH$_3$); 1.88(3H, s, 1-CH$_3$); 3.87, 3.91(total 2H, q, CO—CH$_2$); 7.16(1H, dd, J=8 Hz, 5 Hz, 2 Hz, aromatic H); 7.36(1H, td, J=8 Hz, 5 Hz, aromatic H); 7.44(1H, dd, J=2 Hz, aromatic H);

EXAMPLE 51

Preparation of 2-(2,6-dichlorophenylacetylhydrazono)-2-deoxo-KA-7367A

The procedure in EXAMPLE 41 was repeated except using 30 mg of KA-7367A and 33 mg of 2,6-dichlorophenylacetylhydrazine to provide 59 mg of a final product.

$^1$H-NMR: (CDCl$_3$, TMS) δ; 0.91(3H, t, J=7 Hz, 6'-CH$_3$); 1.40(3H, d, J=7 Hz, 4-CH$_3$); 1.86(3H, s, 1-CH$_3$); 4.32(2H, s, CO—CH$_2$); 7.15(1H, dd, J=9 Hz, 7 Hz, aromatic H); 7.34(2H, m, aromatic H)

EXAMPLE 52

Preparation of 2-(alpha-naphthylacetylhydrazono)-2-deoxo-KA-7367A

The procedure in EXAMPLE 41 was repeated except using 30 mg of KA-7367A and 28 mg of alpha-naphthylacetylhydrazine to provide 43 mg of a final product.

$^1$H-NMR: (CDCl$_3$, TMS) δ; 0.89(3H, t, J=7 Hz, 6'-CH$_3$); 1.38(3H, d, J=7 Hz, 4-CH$_3$); 1.78(3H, s, 1-CH$_3$); 7.45(4H, m, aromatic H); 7.8(2H, m, aromatic H);; 8.08(1H, m, aromatic H)

EXAMPLE 53

Preparation of 2-(4-acetylpiperazinyl-acetylhydrazono)-2-deoxo-KA-7367A

The procedure in EXAMPLE 41 was repeated except using 60 mg of KA-7367A and 58 mg of 4-acetylpiperazinylacetylhydrazine to obtain 58 mg of a final product.

$^1$H-NMR: (CDCl$_3$, TMS) δ; 0.93(3H, t, J=7 Hz, 6'-CH$_3$); 1.42(3H, d, J=7 Hz, 4-CH$_3$); 1.96(3H, s, 1-CH$_3$); 2.11(3H, s, CO—CH$_3$); 3.23(2H, s, N—CH$_2$—CO); 2.62(4H, m, aromatic H); 3.53(2H, m, aromatic H); 3.67(2H, m, aromatic H)

EXAMPLE 54

Preparation of 2-[4-(2,6-dichlorophenylacetyl)-1-piperazinylacetylhydrazino]-2-deoxo-KA-7367A The procedure in EXAMPLE 41 was repeated except using 40 mg of KA-7367A and 68 mg of 4-(2,6-diphenylacetyl)-1-piperazinylacetylhydrazine to obtain 80 mg of a final product.

$^1$H-NMR: (CDCl$_3$, TMS) δ; 0.92(3H, t, J=7 Hz, 6'-CH$_3$); 1.42(3H, d, J=7 Hz, 4-CH$_3$); 1.96(3H, s, 1-CH$_3$); 2.64(4H, m, aromatic H); 3.58(2H, m, aromatic H); 3.72(2H, m, aromatic H); 3.78(2H, s, CO—CH$_2$—N); 7.25(2H, m, aromatic H); 7.42(1H, m, aromatic H)

EXAMPLE 55

Preparation of 2-(2,4-dichlorophenoxyacetylhydrazono)-2-deoxo-KA-7367A

The procedure in EXAMPLE 41 was repeated except using 30 mg of KA-7367A and 33 mg of 2,4-dichlorophenoxyacetylhydrazine to provide 35 mg of a final product.

$^1$H-NMR: (CDCl$_3$, TMS) δ; 0.92(3H, t, J=7 Hz, 6'-CH$_3$); 1.43(3H, d, J=7 Hz, 4-CH$_3$); 2.04(3H, s, 1-CH$_3$); 4.65(2H, s, CO—CH$_2$—N); 6.86(1H, d, J=9 Hz, aromatic H); 7.26(1H, dd, J=3 Hz, aromatic H); 7.43(1H, d, J=3 Hz, aromatic H)

EXAMPLE 56

Preparation of 2-[(N-methyl-N-alpha-naphthylmethylamino)-acetylhydrazino]-2-deoxo-KA-7367A The procedure in EXAMPLE 41 was repeated except using 60 mg of KA-7367A and 79 mg of (N-methyl-N-alphanaphthylmethylamino)-acetylhydrazine to afford 73 mg of a final product.

$^1$H-NMR: (CDCl$_3$, TMS) δ; 0.92(3H, t, J=7 Hz, 6'-CH$_3$); 1.28(3H, d, J=7 Hz, 4-CH$_3$); 1.53(3H, s, 1-CH$_3$); 2.48(3H, s, N-CH$_3$); 3.26(2H, s, N-CH$_2$-naphthyl); 4.03(2H, s, CO—CH$_2$—N); 7.4–7.6(4H, m, aromatic H); 7.85(2H, m, aromatic H); 8.2(1H, m, aromatic H)

EXAMPLE 57

Preparation of 2-[p-(N-methyl-N-alpha-naphthylmethylaminomethyl)-benzoylhydrazono]-2-deoxo-KA-7367A The procedure in EXAMPLE 41 was repeated except using 40 mg of KA-7367A and 70 mg of p-(N-methyl-N-alpha-naphthylmethylaminomethyl)benzoylhydrazine to obtain 14 mg of a final product.

$^1$H-NMR: (CDCl$_3$, TMS) δ; 0.91(3H, t, J=7 Hz, 6'-CH$_3$); 1.98(3H, s, 1-CH$_3$); 2.20(3H, s, N-CH); 3.61(2H, s,

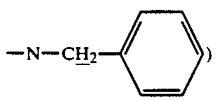

3.95(2H, s,

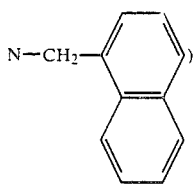

7.35–7.55(6H, m, aromatic H); 7.75–7.9(4H, aromatic H); 8.3(1H, m, aromatic H)

EXAMPLE 58

Preparation of 2-(2,6-dichlorobenzoylhydrazono)-2-deoxo-KA-7367A

The procedure in EXAMPLE 41 was repeated except using 30 mg of KA-7367A and 31 mg of 2,6-dichlorobenzoylhydrazine to obtain 40 mg of a final product.

$^1$H-NMR: (CDCl$_3$, TMS) δ; 0.92(3H, t, J=7 Hz, 6'-CH$_3$); 1.14(3H, d, J=7 Hz, 4-CH$_3$); 1.99(3H, s, 1-CH$_3$); 7.25–7.35(3H, m, aromatic H)

EXAMPLE 59

Preparation of 2-[(2,6-dichlorophenyl)propionylhydrazono]-2-deoxo-KA-7367A

The procedure in EXAMPLE 41 was repeated except using 30 mg of KA-7367A and 35 mg of (2,6-dichlorophenyl)propionylhydrazine to afford 36 mg of a final product.

$^1$H-NMR: (CDCl$_3$, TMS) δ; 0.92(3H, t, J=7 Hz, 6'-CH$_3$); 1.34(3H, d, J=7 Hz, 4-CH$_3$); 1.89(3H, s, 1-CH$_3$); 2.88(2H, m, CO—CH$_2$—CH$_2$); 3.28(2H, m, CO—CH$_2$—CH$_2$); 7.09(1H, dd, J=9 Hz, aromatic H); 7.3(2H, m, aromatic H)

EXAMPLE 60

Preparation of 2-[(2,6-dichlorophenyl)butyrylhydrazono]-2-deoxo-KA-7367A

The procedure in EXAMPLE 41 was repeated except using 20 mg of KA-7367A and 25 mg of (2,6-dichlorophenyl)butyrylhydrazine to afford 19 mg of a final product.

$^1$H-NMR (CDCl$_3$, TMS) δ; 0.92(3H, t, J=7 Hz, 6'-CH$_3$); 1.36(3H, d, J=7 Hz, 4-CH$_3$); 1.89(3H, s, 1-CH$_3$); 1.97(2H, q, J=8 Hz, CO—CH$_2$—CH$_2$—CH$_2$—); 2.76(2H, t, J=8 Hz, CO—CH$_2$—CH$_2$—CH$_2$—); 3.00(2H, m, CO—CH$_2$—CH$_2$—CH$_2$—) 7.07(1H, dd, J=9 Hz, 7 Hz, aromatic H); 7.3(2H, m, aromatic H);

EXAMPLE 61

Preparation of 2-[(2,6-difluorophenyl)acetylhydrazono]-2-deoxo-KA-7367A

The procedure in EXAMPLE 41 was repeated except using 65 mg of KA-7367A and 61 mg of (2,6-difluorophenyl)acetylhydrazine to obtain 73 mg of a final product.

$^1$H-NMR: (CDCl$_3$, TMS) δ; 0.91(3H, t, J=7 Hz, 6'-CH$_3$); 1.37(3H, d, J=7 Hz, 4-CH$_3$); 1.88(3H, s, 1-CH$_3$); 4.42(2H, s,

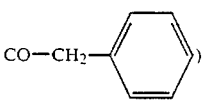

6.9–7.3(5H, m, —CH=CH—, aromatic H)

EXAMPLE 62

Preparation of 2-[(2,6-dimethoxyphenyl)acetylhydrazono]-2-deoxo-KA-7367A

The procedure in EXAMPLE 41 was repeated except using 14 mg of KA-7367A and 15 mg of (2,6-dimethoxyphenyl)acetylhydrazine to obtain 8 m of a final product.

$^1$H-NMR (CDCl$_3$, TMS) δ; 0.91(3H, t, J=7 Hz, 6'-CH$_3$); 1.33, 1.38(total 3H, t, J=7 Hz, 4-CH$_3$); 1.72, 1.86(total 3H, s, 1-CH$_3$); 3.77, 3.85(total 6H, s, OCH$_3$); 6.5–6.6(2H, m, aromatic H); 7.2(1H, m, aromatic H)

EXAMPLE 63

Preparation of 2-(2,6-dinitrophenylhydrazono)-·2-deoxo-KA-7367A

The procedure in EXAMPLE 41 was repeated except using 50 mg of KA-7367A and 50 mg of 2,6-dinitrophenylhydrazine to obtain 71 mg of a final product.

$^1$H-NMR (CDCl$_3$, TMS) δ; 0.92(3H, t, J=7 Hz, 6'-CH$_3$); 1.47(3H, d, J=7 Hz, 4-CH$_3$); 2.12(3H, s, 1-CH$_3$); 7.90(1H, m, aromatic H); 8.28(1H, m, aromatic H); 9.09(1H, m, aromatic H)

EXAMPLE 64

Preparation of 2-methoxycarbonylhydrazono-2-deoxo-KA-7367A

The procedure in EXAMPLE 41 was repeated except using 20 mg of KA-7367A and 9.1 mg of methyl carbazinate to afford 13 mg of a final product.

$^1$H-NMR: (CDCl$_3$, TMS) δ; 0.92(3H, t, J=7 Hz, 6'-CH$_3$); 1.37(3H, d, J=7 Hz, 4-CH$_3$); 1.89(3H, s, 1-CH$_3$); 3.82(3H, s, OCH$_3$); 4.89(1H, 1, J=7 Hz, 3-CH$_3$)

EXAMPLE 65

Preparation of 2-sulfophenylhydrazono-2-deoxo-KA-7367A monosodium salt:

The procedure in EXAMPLE 41 was repeated except using 100 mg of KA-7367A and 106 mg of monosodium p-hydrazonobenzenesulfonate to afford 196 mg of a final product.

$^1$H-NMR: (CDCl$_3$, TMS) δ; 0.92(3H, t, J=7 Hz, 6'-CH$_3$); 1.32(3H, d, J=7 Hz, 4-CH$_3$); 1.64(3H, s, 1-CH$_3$); 7.73(2H, m, aromatic H); 7.95(2H, m, aromatic H)

EXAMPLE 66

Preparation of 2-phenylacetylhydrazono-2-deoxo-KA-7367A

The procedure in EXAMPLE 41 was repeated except using 50 mg of KA-7367A and 38 mg of phenylacetylhydrazine to afford 55 mg of a final product.

$^1$H-NMR: (CDCl$_3$, TMS) δ; 0.92(3H, t, J=7 Hz, 6'-CH$_3$); 1.40(3H, d, J=7 Hz, 4-CH$_3$); 1.88(3H, s,,1-CH$_3$); 3.96(2H, s,

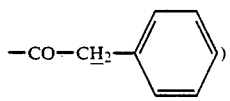

6.9–7.2(5H, m, aromatic H)

EXAMPLE 67

Preparation of 2-(2-furylcarbonylhydrazono)-2-deoxo-KA-7367A

The procedure in EXAMPLE 41 was repeated except using 40 mg of KA-7367A and 30 mg of 2-furylcarbonylhydrazine to obtain 37 mg of a final product.

$^1$H-NMR: (CDCl$_3$, TMS) δ; 0.92(3H, t, J=7 Hz, 6'-CH$_3$); 1.46(3H, d, J=7 Hz, 4-CH$_3$); 1.98(3H, s, 1-CH$_3$); 7.0–7.2(3H, m, aromatic H)

EXAMPLE 68

Preparation of 2-thenoylhydrazono-2-deoxo-KA-7367A

The procedure in EXAMPLE 41 was repeated except using 40 mg of KA-7367A and 35 mg of thenoylhydrazine to obtain 30 mg of a final product.

$^1$H-NMR: (CDCl$_3$, TMS) δ; 0.92(3H, t, J=7 Hz, 6'-CH$_3$); 1.48(3H, d, J=7 Hz, 4-CH$_3$); 2.00(3H, s, 1-CH$_3$); 7.02–7.12(3H, m, aromatic H)

EXAMPLE 69

Preparation of 2-thiocarbonohydrazono-2-deoxo-KA-7367A

The procedure in EXAMPLE 41 was repeated except using 60 mg of KA-7367A and 40 mg of thiocarbonohydrazide to obtain 38 mg of a final product.

$^1$H-NMR (CDCl$_3$, TMS) δ; 0.93(3H, t, J=7 Hz, 6'-CH$_3$); 1.37(3H, d, J=7 Hz, 4-CH$_3$); 1.95(3H, s, 1-CH$_3$); 2.23(2H, 1, J=7 Hz, 3 -CH$_3$); 4.75(1H, q, J=7 Hz, 3-CH); 6.9–7.1(2H, m, —CH=CH—)

EXAMPLE 70

Preparation of 2-isonicotinoylhydrazono-2-deoxo-KA-7367A

The procedure in EXAMPLE 41 was repeated except using 100 mg of KA-7367A and 112 mg of isonicotinoylhydrazine to obtain 119 mg of a final product.

$^1$H-NMR: (CDCl$_3$, TMS) δ; 0.93(3H, t, J=7 Hz, 6'-CH$_3$); 1.54(3H, d, J=7 Hz, 4-CH$_3$); 2.24(3H, s, 1-CH$_3$); 5.22(1H, q, J=7 Hz, 3-CH); 6.9–7.1(2H, m, —CH=CH—); 7.67(2H, m, aromatic H); 8.74(2H, m, aromatic H)

EXAMPLE 71

Preparation of 2-nicotinoylhydrazono-2-deoxo-KA-7367A

The procedure in EXAMPLE 41 was repeated except using 200 mg of KA-7367A and 200 mg of nicotinoylhydrazine to afford 206 mg of a final product.

$^1$H-NMR: (CDCl$_3$, TMS) δ; 0.93(3H, t, J=7 Hz, 6'-CH$_3$); 1.53(3H, d, J=7 Hz, 4-CH$_3$); 2.24(3H, s, 1-CH$_3$); 5.22(1H, q, J=7 Hz, 3-CH); 6.9–7.1(2H, m, —CH=CH—); 7.45(1H, dd, J=5 Hz, 7 Hz, aromatic H); 8.18(1H, dt, J=2 Hz, 2 Hz, 8 Hz, aromatic H); 8.67(1H, dd, J=2 Hz, 5 Hz, aromatic H); 9.06(1H, br.s, aromatic H)

EXAMPLE 72

Preparation of 2-(o-chlorophenylacetylhydrazono)-2-deoxo-KA-7367A

The procedure in EXAMPLE 41 was repeated except using 50 mg of KA-7367A and 48 mg of o-chlorophenylacetylhydrazine to afford 64 mg of a final product.

$^1$H-NMR: (CDCl$_3$, TMS) δ; 0.92(3H, t, J=7 Hz, 6'-CH$_3$); 1.39(3H, d, J=7 Hz, 4-CH$_3$); 1.83(3H, s, 1-CH$_3$); 2.23(2H, q,,3'-CH$_2$); 4.11(2H, s,

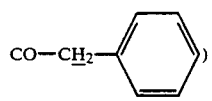

4.83(1H, q, J=7 Hz, 3-CH)

EXAMPLE 73

Preparation of 2-(m-chlorophenylacetylhydrazono)-2-deoxo-KA-7367A

The procedure in EXAMPLE 41 was repeated except using 25 mg of KA-7367A and 24 mg of m-chlorophenylacetylhydrazine to afford 27 mg of a final product.

$^1$H-NMR: (CDCl$_3$, TMS) δ; 0.92(3H, t, J=7 Hz, 6'-CH$_3$); 1.40(3H, d, J=7 Hz, 4-CH$_3$); 1.38(3H, s, 1-CH$_3$); 2.23(2H, q, 3'-CH$_3$); 3.93(2H, s,

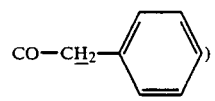

4.82(1H, q, J=7 Hz, 3-CH); 6.9–7.1(2H, m, —CH=CH—)

EXAMPLE 74

Preparation of 2-(p-chlorophenylacetylhydrazono)-2-deoxo-KA-7367A

The procedure in EXAMPLE 41 was repeated except using 25 mg of KA-7367A and 24 mg of p-chlorophenylacetylhydrazine to afford 30 mg of a final product.

$^1$H-NMR: (CDCl$_3$, TMS) δ; 0.92(3H, t, J=7 Hz, 6'-CH$_3$); 1.39(3H, d, J=7 Hz, 4-CH$_3$); 1.87(3H, s, 1-CH$_3$); 2.23(2H, q, 3'-CH$_2$); 3.93(2H, s,

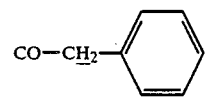

4.90(1H, q, J=7 Hz, 3-CH); 6.9–7.1(2H, m, —CH=CH—);

EXAMPLE 75

Preparation of 2-[alpha-(1-imidazolyl)-p-chlorophenylacetylhydrazono]-2-deoxo-KA-7367A The procedure in EXAMPLE 41 was repeated except using 150 mg of KA-7367A and 178 mg of alpha-(1-imidazolyl)-p-chlorophenylacetylhydrazine to obtain 180 mg of a final product.

$^1$H-NMR: (CDCl$_3$, TMS) δ; 0.93(3H, t, J=7 Hz, 6'-CH$_3$); 1.28, 1.29(total 3H, d, J=7 Hz, 4-CH$_3$); 1.90, 1.91(total 3H, s, 1-CH$_3$); 2.21, 2.23(total 2H, 3'-CH$_2$); 4.68, 4.71(total 1H, q, 3-CH); 6.80(1H, s, aromatic H); 6.9–7.1(2H, m, —CH=CH—)

EXAMPLE 76

Preparation of 2-[alpha-(2-oxo-1-pyridyl)-p-chlorophenylacetylhydrazono]-2-deoxo-KA-7367A The procedure in EXAMPLE 41 was repeated except using 85 mg of KA-7367A and 96 mg of alpha-(2-oxo-1-pyridyl)-p-chlorophenylacetylhydrazine to obtain 45 mg of a final product.

$^1$H-NMR: (CDCl$_3$, TMS) δ; 0.92(3H, t, J=7 Hz, 6'-CH$_3$); 1.18, 1.14(total 3H, d, J=7 Hz, 4-CH$_3$); 1.82, 1.85(total 3H, s, 1-CH$_3$); 2.21(2H, q, 3'-CH$_2$); 4.64, 4.66(total 1H, q, J=7 Hz, 3-CH); 6.8–7.0(2H, m, —CH=CH—)

EXAMPLE 77

Preparation of 2-(p-chlorocinnamoylhydrazono)-2-deoxo-KA-7367A

The procedure in EXAMPLE 41 was repeated except using 150 mg of KA-7367A and 983 mg of p-chlorocinnamoylhydrazine to obtain 80 mg of a final product.

$^1$H-NMR: (CDCl$_3$, TMS) δ; 0.92(3H, t, J=7 Hz, 6'-CH$_3$); 1.42(3H, d, J=7 Hz, 4-CH$_3$); 2.01(3H, s, 1-CH$_3$); 2.22(2H, q, 3'-CH$_2$); 4.00(1H, q, J=7 Hz, 3-CH); 6.0–7.1(2H, m, —CH=CH—)

EXAMPLE 78

Preparation of 2-(2,4'-dichlorodiphenylacetylhydrazono)-2-deoxo-KA-7367A

The procedure in EXAMPLE 41 was repeated except using 85 mg of KA-7367A and 104 mg of 2,4'-dichlorodiphenylacetylhydrazine to obtain 58 mg of a final product.

$^1$H-NMR: (CDCl$_3$, TMS) δ; 0.92(3H, t, J=7 Hz, 6'-CH$_3$); 1.24(3H, d, J=7 Hz, 4-CH$_3$); 1.77(3H, s, 1-CH$_3$); 2.22(2H, q, 3'-CH$_2$); 4.78(1H, q, J=7 Hz, 3-CH); 6.31(1H, s, aromatic H); 6.9–7.1(2H, m, —CH=CH—)

EXAMPLE 79

Preparation of 2-(2,4-dichlorodiphenylacetylhydrazono)-2-dioxo-KA-7367A

The procedure in EXAMPLE 41 was repeated except using 120 mg of KA-7367A and 151 mg of 2,4-dichlorodiphenylacetylhydrazine to afford 161 mg of a final product.

$^1$H-NMR: (CDCl$_3$, TMS) δ; 0.91(3H, t, J=7 Hz, 6'-CH$_3$); 1.23, 1.27(3H, d, J=7 Hz, 4-CH$_3$); 1.77(3H, s, 1-CH$_3$); 2.22(2H, q, 3'-CH$_2$); 4.70, 4.73(1H, q, J=7 Hz, 3-CH); 5.31(1H, s, aromatic H); 6.9–7.1(2H, m, —CH=CH—)

EXAMPLE 80

Preparation of 2-diphenylacetylhydrazono-2-deoxo-KA-7367A

The procedure in EXAMPLE 41 was repeated except using 60 mg of KA-7367A and 60 mg of diphenylacetylhydrazine to afford 70 mg of a final product.

$^1$H-NMR: (CDCl$_3$, TMS) δ; 0.92(3H, t, J=7 Hz, 6'-CH$_3$); 1.31(3H, d, J=7 Hz, 4-CH$_3$); 1.82(3H, s, 1-CH$_3$); 2.23(2H, q, 3'-CH$_2$); 4.77(1H, q, J=7 Hz, 3-CH); 6.00(1H, s, aromatic H); 6.9–7.1(2H, m, —CH=CH—)

EXAMPLE 81

Preparation of 2-[bis(2,4-dichlorophenyl)acetylhydrazono]-2-deoxo-KA-7367A

The procedure in EXAMPLE 41 was repeated except using 20 mg of KA-7367A and 40 mg of bis(2,4-dichlorophenyl)-acetylhydrazine to afford 19 mg of a final product.

$^1$H-NMR: (CDCl$_3$, TMS) δ; 0.92(3H, t, J=7 Hz, 6'-CH$_3$); 1.23(3H, d, J=7 Hz, 4-CH$_3$); 1.78(3H, s, 1-CH$_3$); 2.23(2H, q, 3'-CH$_2$); 4.66(1H, q, J=7 Hz, 3-CH); 6.49(1H, s, aromatic H); 6.8–7.0(2H, m, —CH=CH—)

EXAMPLE 82

Preparation of 2-(2,4,4'-trichlorodiphenylacetylhydrazono)-2-deoxo-KA-7367A

The procedure in EXAMPLE 41 was repeated except using 60 mg of KA-7367A and 48 mg of 2,4,4,-trichlorodiphenylacetylhydrazine to afford 23 mg of a final product.

$^1$H-NMR: (CDCl$_3$, TMS) δ; 0.92(3H, t, J=7 Hz, 6'-CH$_3$); 1.25, 1.29(total 3H, d, J=7 Hz, 4-CH$_3$); 1.82(3H, s, 1-CH$_3$); 2.21, 2.23(2H, q, 3'-CH$_2$); 4.72, 4.73(1H, q, J=7 Hz, 3-CH); 6.23(1H, s, aromatic H); 6.9–7.1(2H, m, —CH=CH—)

EXAMPLE 83

Preparation of 2-methoxycarbonylhydrazono-2-deoxo-KA-7367A

The procedure in EXAMPLE 41 was repeated except using 100 mg of KA-7367A and 60 mg of methoxycarbonylethylhydrazine to obtain 37 mg of a final product.

$^1$H-NMR: (CDCl$_3$, TMS) δ; 0.92(3H, t, J=7 Hz, 6'-CH$_3$); 1.33(3H, d, J=7 Hz, 4-CH$_3$); 1.78(3H, s, 1-CH$_3$); 2.22(2H, q, 3'-CH$_2$); 2.59(2H, t, J=6 Hz, NCH$_2$CH$_2$CO); 3.45(2H, t, J=6 Hz, NCH$_2$CH$_2$CO); 3.70(3H, s, OCH$_3$); 4.76(1H, q, 3-CH); 6.9–7.1(2H, m, —CH=CH—)

EXAMPLE 84

Preparation of 2-[2-(p-chlorophenyl)-2-methoxycarbonylethylhydrazono]-2-deoxo-KA-7367A The procedure in EXAMPLE 41 was repeated except using 100 mg of KA-7367A and 70 mg of 2-(p-chlorophenyl)-2-methoxyethylhydrazine to obtain 75 mg of a final product.

$^1$H-NMR: (CDCl$_3$, TMS) δ; 0.92(3H, t, J=7 Hz, 6'-CH$_3$); 1.35(3H, d, J=7 Hz, 4-CH$_3$); 1.62(3H, s, 1-

CH$_3$); 2.22(2H, q, 3'-CH$_2$); 3.3-3.8(3H, m, —CH$_2$—CH—); 3.66(3H, s, OCH$_3$); 4.70(1H, q, 3-CH); 6.9-7.1(2H, m, —CH=CH—) 7.1-7.3(4H, m, aromatic H)

PREPARATION EXAMPLE 1

Capsules for administration to humans

| Compound in EXAMPLE 4 | 500 g |
|---|---|
| Microcrystal cellulose | 90 |
| Talc | 30 |

The above components were uniformly mixed in a usual manner and the mixture was filled in 1000 No. 0 capsules.

| Compound in EXAMPLE 3 | 2.0 g |
|---|---|
| White soft paraffin | 25.0 |
| Stearyl alcohol | 25.0 |
| Propylene glycol | 12.0 |
| Sodium lauryl sulfate | 1.5 |
| Ethyl p-hydroxybenzoate | 0.5 |
| Deionized water | 34.0 |

The above components were uniformly mixed in a usual manner and the mixture was formed into a cream.

PREPARATION EXAMPLE 3

Emulsifiable concentrate for agricultural and horticultural use

| Compound in EXAMPLE 43 | 250 g |
|---|---|
| Epoxidized vegetable oil | 25 |
| Mixture of alkylaryl sulfonate, polyglycol ether and aliphatic alcohol | 100 |
| Dimethylformamide | 50 |
| Xylene | 575 |

The above components were uniformly mixed in a usuall manner and the mixture was formed into an emulsifiable concentrate. This is diluted with water into an emulsion.

INDUSTRIAL AVAILABILITY

The compounds in this invention are excellent in antifungal activity to fungi that infect warm-blooded animals including humans and agricultural and horticultural crops and in stability, and are useful as agents for prevention, treat ment or therapy of infectious diseases caused by these fungi or control of plant diseases caused by these fungi.

We claim:

1. An azoxy compound represented by formula

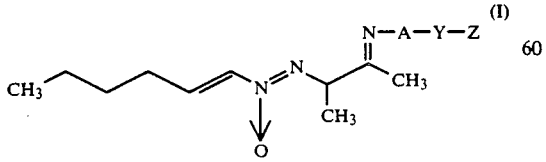

wherein

A denotes —O—, —OCO—, —NH—, —NHCO—, —HNCS— or

Y denotes a single bond or a linear or branched alkylene group with 1 to 6 carbon atoms or a linear or branched alkenylene group with 2 to 6 carbon atoms, and said alkylene or alkenylene group may optionally be substituted by a halogen atom, a phenyl group or a halophenyl group, Z denotes a hydrogen atom, an alkoxy group with 1 to 5 carbon atoms, a carboxyl group, an alkoxycarbonyl group with 2 to 6 carbon atoms, a phenyl group that may optionally have 1 to 3 substituents selected from a halogen atom, an alkoxy group with 1 to 5 carbon atoms, a carboxyl group, a nitro group, a sulfonyl group and a N-methyl-N-alpha-naphthylmethylaminomethyl group, a phenoxy group in which a benzene ring may optionally be substituted by 1 to 3 halogen atoms, a naphthyl group, a cyano group, a pyridyl group, an oxopyridyl group, a imidazolyl group, a furyl group, a thienyl group or a group of formula

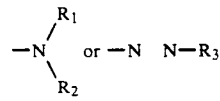

R$_1$ and R$_2$ are the same or different and each denotes a hydrogen atom, an alkyl group with 1 to 3 carbon atoms, a phenyl group, a naphthyl group, a phenylalkyl group with 7 to 10 carbon atoms, a naphthylalkyl group with 11 to 14 carbon atoms or an amino group, and R$_3$ denotes an alkyl group with 1 to 3 carbon atoms, an alkoxy group with 1 to 3 carbon atoms, a benzoyl group or an alkanoyl group with 2 to 6 carbon atoms that may optionally be substituted by a phenyl group or a halophenyl group, provided when A is the group of formula

Z is a hydrogen atom, or a salt thereof.

2. The compound of claim 1 wherein

A is —O—,

Y is a single bond, or a linear or branched alkylene group with 1 to 4 carbon atoms or a linear alkenylene group with 2 to 4 carbon atoms that may obtionally be substituted by 1 to 3 halogen atoms or halophenyl groups, Z is a hydrogen atom, an alkoxy group with 1 to 3 carbon atoms, a carbonyl group, a phenyl group that may optionally have 1 to 2 substituents selected from the group consisting of a halogen atom and a carboxyl group, a cyano group or a group of formula

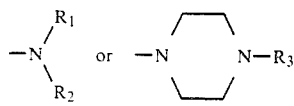

$R_1$ and $R_2$ are the same or different and each is an alkyl group with 1 to 3 carbon atoms, and
$R_3$ is a benzoyl group.

3. The compound of claim 1 wherein
A is —OCO—, p1 Y is a single bond or a linear alkylene group with 1 to 4 carbon atoms, and
Z is a hydrogen atom, an alkoxy group with 1 to 3 carbon atoms or a phenyl group that may optionally be substituted by 1 to 3 halogen atoms.

4. The compound of claim 1 wherein
A is —NH—,
Y is a single bond or a linear alkylene group with 1 to 4 carbon atoms that may optionally be substituted by a phenyl group or a halophenyl group, and
Z is a hydrogen atom, an alkoxycarbonyl group with 2 to 4 carbon atoms or a phenyl group that may optionally be substituted by a sulfonyl group.

5. The compound of claim 1 wherein
A is —NHCO—,
Y is a single bond or a linear alkylene or alkenylene group with 1 to 4 carbon atoms that may optionally be substituted by 1 to 3 halogen atoms, phenyl groups or halophenyl groups,
Z is a hydrogen atom, an alkoxy group with 1 to 3 carbon atoms, a phenyl group that may optionally have 1 to 2 substituents selected from a halogen atom, an alkoxy group with 1 to 3 carbon atoms, a nitro group and a N-methyl-N-alpha-naphthylmethylaminomethyl group, a phenoxy group in which a benzene ring may optionally be substituted with 1 to 2 halogen atoms, a naphthyl group, a pyridyl group, an oxopyridyl group, an imidazolyl group, a furyl group, a thienyl group or a group of formula

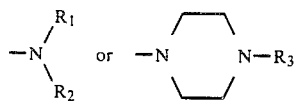

$R_1$ and $R_2$ are the same or different and each is a hydrogen atom, an alkyl group with 1 to 3 carbon atoms, a phenyl group or a naphthylalkyl group with 11 to 12 carbon atoms, and
$R_3$ is an alkoxy group with 1 to 3 carbon atoms or an alkanoyl group with 2 to 4 carbon atoms that may optionally be substituted by a halophenyl group.

6. The compound of claim 1 wherein
A is —NHCS—,
Y is a single bond,
Z is

and $R_1$ and $R_2$ are the same or different and each is a hydrogen atom, an alkyl group with 1 to 3 carbon atoms, a phenyl group or an amino group.

7. The compound of claim 1 wherein
A is

Y is a linear alkylene group with 1 to 4 carbon atoms, and
Z is a hydrogen atom.

8. The compound of claim 1 which is selected from the group consisting of
2-hydroxyimino-2-deoxo-KA-7367A,
2-methoxyimino-2-deoxo-KA-7367A,
2-(2-ethoxy-ethoxyimino)-2-deoxo-KA-7367A,
2-carboxymethoxyimino-2-deoxo-KA-7367A,
2-(1-carboxy-1-methylethoxyimino)-2-deoxo-KA-7367A,
2-acetoxyimino-2-deoxo-KA-7367A,
2-benzoyloxyimino-2-deoxo-KA-7367A,
2-(p-chlorobenzoyloxyimino)-2-deoxo-KA-7367A,
2-semicarbazono-2-deoxo-KA-7367A,
2-thiosemicarbazono-2-deoxo-KA-7367A,
2-acetylhydrazono-2-deoxo-KA-7367A,
2-(1-imidazolylacetylhydrazono)-2-deoxo-KA-367A,
2-(3-pyridylacetylhydrazono)-2-deoxo-KA-7367A,
2-(2-(2,4-dichlorophenylacetylhydrazono)-2-deoxo-KA-7367A,
2-(alpha-naphthylacetylhydrazono)-2-deoxo-KA-7367A,
2-(4-acetylpiperazinyl-acetylhydrazono)-2-deoxo-KA-7367A,
2-[4-(2,6-dichlorophenylacetyl)-1-piperazinylacetylhydrazono]-2-deoxo-KA-7637A,
2-[(2,6-difluorophenyl)acetylhydrazono]-2deoxo-KA-7367A,
2-[2,6-dimethoxyphenyl)acetylhydrazono]-2-deoxo-KA-7367A,
2-(2-furylcarbonylhydrazono)-2-deoxo-KA-7367A,
2-thenoylhydrazono-2-deoxo-KA-7367A,
2-isonicotinoylhydrazono-2-deoxo-KA-7367A,
2-nicotinoylhydrazono-2-deoxo-KA-7367A,
2-(p-chlorophenylacetylhydrazono)-2-deoxo-KA-7367A,
2-(2,4'-dichlorodiphenylacetylhydrazono)-2-deoxo-KA-7367A, and
2-(2,4-dichlorodiphenylacetylhydrazono)-2-deoxo-KA-7367A.

9. A process for producing the compound of formula (I) or a salt thereof which comprises reacting KA-7367A represented by formula

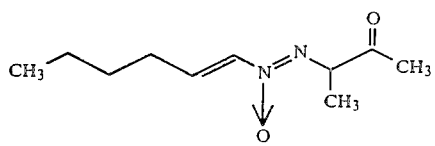

with a compound represented by formula $$H_2N—A13\ Y13\ Z \qquad (II)$$

or a salt thereof and optionally converting the product into a salt.

10. An antifungal composition comprising an antifungally effective amount of the compound of formula (I) or a salt thereof as defined in claim 1 and an adjuvant.

11. A method for treatment of a warm-blooded animal infested with fungi which comprises administering to the animal an antifungally effective amount of a compound of formula (I) or a pharmaceutically acceptable salt thereof as defined in claim 1.

12. A fungicidal method which comprises applying an antifungally effective amount of a compound of formula (I) or a salt thereof as defined in claim 1 to a habitat area of fungi, soil or plant stems and leaves.

* * * * *